United States Patent [19]

Navarrini et al.

[11] Patent Number: 5,103,050

[45] Date of Patent: Apr. 7, 1992

[54] PROCESS FOR PREPARING PERFLUOROALKENYL-SULFONYL FLUORIDES

[75] Inventors: Walter Navarrini; Silvana Modena, both of Milan, Italy

[73] Assignee: Ausimont S.r.l., Milan, Italy

[21] Appl. No.: 515,041

[22] Filed: Apr. 26, 1990

[30] Foreign Application Priority Data

Apr. 28, 1989 [IT] Italy .................. 20339 A/89

[51] Int. Cl.⁵ .......................... C07C 309/80
[52] U.S. Cl. .................................. 562/825
[58] Field of Search ................ 562/834, 825

[56] References Cited

U.S. PATENT DOCUMENTS 3,041,317  6/1962  Gibbs et al. .................. 562/825
4,834,922  5/1989  Ezzell et al. .................. 562/825

FOREIGN PATENT DOCUMENTS 60-36454  2/1985  Japan .................. 562/825

*Primary Examiner*—Alan Siegel
*Assistant Examiner*—Margaret Argo
*Attorney, Agent, or Firm*—Stevens, Davis, Miller & Mosher

[57] ABSTRACT

A continuous process for preparing perfluoroalkenyl sulfonyl fluorides (I)

$$R_f-CF=CF-SO_2F \qquad (I)$$

wherein: $R_f$ is selected from the group consisting of F and a perfluoroalkyl radical of from 1 to 9 carbon atoms is disclosed, in which as the starting compound a sultone (II)

$$R_f-CF_2-\underset{|}{CF}-\underset{|}{CF_2} \qquad (II)$$
$$\phantom{R_f-CF_2-}SO_2-O$$

is used.

The starting compound is placed into contact with a reactant selected from the group consisting of oxides and carbonates of an element of the Groups IA, IIA and IIB, and of the oxides of an element of the Groups IIIA and IVA of the Periodic Table of the Elements, and their mixtures, at a temperature comprised within the range of from 150° to 450° C., and the compound (I) is recovered from the reaction effluent.

8 Claims, No Drawings

PROCESS FOR PREPARING PERFLUOROALKENYL-SULFONYL FLUORIDES

DESCRIPTION OF THE INVENTION

The present invention relates to a new process for the synthesis of perfluoroalkenyl-sulfonyl fluorides, in particular of perfluorovinyl-sulfonyl fluoride.

These perfluorinated compounds, which contain the sulfonyl function, are monomers useful for preparing high-molecular-weight polymers which find several uses.

In U.S. Pat. No. 3,041,317, a process is disclosed for the synthesys of perfluoroalkenyl-sulfonyl fluorides of formula $$R_f\text{---}CF=CF\text{---}SO_2F$$

wherein $R_f$ is F, or a perfluoroalkyl radical or an omega-hydroperfluoroalkyl radical. The starting products for said synthesis are 2-hydro-perfluoroalkyl-sulfonyl fluorides of general formula $$R_f\text{---}CF_2\text{---}CFH\text{---}SO_2F$$

which are dehydrofluorinated in order to yield perfluoroalkenyl-sulfonyl fluorides in a plant operating under reduced pressure, inside which a stream of reactants flows on a catalyst constituted by chrome oxide supported on KCl, at temperatures comprised within the range of from 450° to 630° C.

In particular for vinyl-sulfonyl fluoride, the reaction is carried out at temperatures comprised within the range of from 508° to 517° C. with a conversion of 51% and a yield of 61%, as referred to the converted reactants, per each individual pass.

R. E. Banks in J. Chem. Soc. (C), 1966 reports about a synthesis of perfluorovinyl-sulfonyl fluoride in which synthesis a catalyst and operating conditions are used, which are exactly the same as disclosed in U.S. Pat. No. 3,041,317, with the only difference that the catalytic bed is pre-heated at 510° C. before the synthesis test is carried out.

In the paper by R. E. Banks, the general reactivity of the same molecule is furthermore described.

In both of the above descriptions, the starting products are 2-hydro-perfluoro-sulfonyl fluorides having the general formula $$R_f\text{---}CHF\text{---}CF_2\text{---}SO_2F$$

which are synthetized by means of the controlled hydrolysis of the relevant sultones of formula

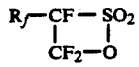

as taught by D. C. England in J. Amer. Chem. Soc. 1960, 82, 6181.

The main object of the present invention is of providing a new process for preparing perfluoroalkenyl-sulfonyl fluorides, which can be carried out under advantageous temperature and pressure conditions from the economic viewpoint, as compared to the processes known from the prior art.

Another object of the present invention is of providing a simplified process, which can be carried out with a smaller number of operating steps than the processes known from the prior art.

A further object is of providing a process which uses easily available and cheap catalysts.

Finally, still a further object of the present invention is of providing a process which supplies high yields of desired perfluoroalkenyl-sulfonyl fluorides.

These and still other objects which will be clear from the following disclosure are achieved by a process, according to the instant invention, for preparing perfluoroalkenyl sulfonyl fluorides having the general formula (I)

$$R_f\text{---}CF=CF\text{---}SO_2F \qquad (I)$$

wherein: $R_f$ is selected from the group consisting of F and a perfluoroalkyl radical of from 1 to 9 carbon atoms, which process consists in bringing into contact, at a temperature within the range of from 150° to 450° C., a starting compound comprising the β-sultone of a 2-hydroxy-1-perfluoroalkyl-1,2,2-trifluoroethane-sulfonic acid having formula (II):

with a reactant selected from the group consisting of oxides and carbonates of an element of the Groups IA, IIA and IIB, and of the oxides of an element of the Groups IIIA and IVA of the Periodic Table of the Elements, and their mixtures, and recovering the desired compound of formula (I) from the reaction effluent.

The present Applicants surprisingly found that, when the reactants and the operating conditions according to the instant invention are used, a perfluoroalkenyl-sulfonyl fluoride (I) can be directly synthetized by starting from a β-sultone (II), without having to pass through further intermediate steps, such as, e.g., the hydrolysis required by the processes known from the prior art.

The reactant used in the instant process is constituted by oxides or carbonates of the above mentioned elements, among which CaO, SiO$_2$, MgO, ZnO, Na$_2$CO$_3$ and CaCO$_3$ can be cited for exemplifying purposes.

The reactions on which the instant invention process is based can be illustrated for exemplifying purposes, relatively to the use of CaO or CaCO$_3$, as follows:

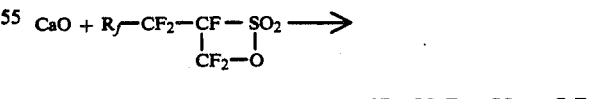

$$R_f\text{---}CF=CF\text{---}SO_2F + CO_2 + CaF_2$$

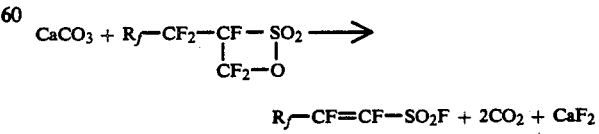

$$R_f\text{---}CF=CF\text{---}SO_2F + 2CO_2 + CaF_2$$

The amount of reactant used is at least the stoichiometric amount required by the above reactions, but it is preferably in excess over said stoichiometric amount, also according to the degree of comminution of the reactant.

The reactant is advantageously submitted to a preliminary activation by being placed into contact with the starting compound before the true process is started.

The process according to the present invention can be advantageously carried out continuously under atmospheric pressure, although also pressures lower or higher than atmospheric pressure can be used as well.

The process temperature can be comprised within the range of from 150° to 450° C., and preferably within the range of from 180° to 280° C.

The process is suitably carried out by causing a stream of an inert gas carrier saturated with vapours of the sultone used as the starting product, to pass or flow on a bed of the reactant contained inside a glass or steel column reactor.

As the inert gas carrier, nitrogen is preferably used.

The process is carried out under anhydrous conditions, with both nitrogen and the reactant bed being preliminarily thoroughly dried; the reactant bed is thoroughly dried by being heated at about 300°-330° C. for a few hours.

In the reactor, a packing of a particulate silicious material, with small particle size, is preferably used in addition to the reactant bed.

Flow rate values of the carrier and reactant stream are used, such as to secure a stay time of the starting compound inside the reactor, in the range of from 3 to 30 seconds.

The effluent from the reactor is condensed at a temperature comprised within the range of from 0° to −196° C. in order to separate the reaction products from nitrogen, which is sent to the discharge stack.

The condensate is distilled under reduced pressure, and the vapours are condensed in a first condenser at a higher temperature, e.g., at a temperature of from −100° to −20° C. in order to recover the desired product perfluoroalkenyl-sulfonyl fluoride, and then in a second condenser at −110° C. in order to recover $SO_2$ produced. The other byproducts, such as $CO_2$ and $SiF_4$, as well as any decomposition products, such as $CF_3COF$ or $C_2F_4$, are removed by the dynamic vacuum during the same distillation.

Complete conversions of the starting compound are obtained, with yields, defined as the ratio of the mols of the desired product to the reacted mols of starting compound, as high as of the order of from 65 to 75%.

The process according to the present invention is particularly useful in order to prepare compounds of formula (I), wherein $R_f$ is F or a perfluoroalkyl radical with 1 to 3 carbon atoms, in particular a trifluoromethyl or perfluoroethyl radical.

The following examples are illustrative of preferred forms of embodiment of the present invention, and in no way such examples should be construed as being limitative of the scope of the present invention, as herein disclosed and as claimed in the hereto appended claims.

EXAMPLE I

In a continuous working plant, 3.2 g (13.5 mmol) of the sultone of 2-hydroxy-1-trifluoromethyl-1,2,2-trifluoroethane-sulfonic acid of formula

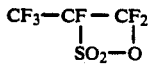

is charged to a loading "U"-shaped trap.

Said loading trap is then put into communication with the continuous plant by means of valves.

A stream of preliminarily thoroughly dried nitrogen is made to flow at the flowrate of 18 litres/hour through the loading trap kept at the temperature of −35° C. throughout the test time.

Nitrogen saturated with the vapours of the sultone used as the starting product flows through the reactor kept at the temperature of 210° C.

During about 3 hours, all of the starting product is transported through the reactor, which is constituted by a steel column of 3.0 cm of diameter, packed with 100 g of calcium oxide and 100 g of steel small tubes; the so constituted reactive bed is preliminarily thoroughly desiccated by being kept at the temperature of 320° C. for 4 hours, and is then activated by causing 13.5 mmol of β-sultone of perfluoropropene to flow through it under the same operating conditions as disclosed hereinabove.

The effluent gases from the reactor are caused to flow through two traps maintained at the temperature of −196° C. so as to condense all of the reaction products, whereas the nitrogen carrier gas flows to the discharge stack.

The raw reaction product contained in the two collection traps is distilled under the pressure of $10^{-3}$ torr. The vapours coming from the still kettle are caused to flow through cold traps respectively kept at the temperatures of −80° and −110° C.

Inside the trap at −110° C., 0.2 mmol of $SO_2$ condenses; in the traps at −80° C. 9.4 mmol of desired trifluorovinyl-sulfonyl fluoride product

condenses. $CO_2$, and any decomposition products, such as, e.g., $CF_3COF$ and $C_2F_4$ are removed by the dynamic vacuum during the same distillation.

The conversion of the starting product is complete.

The yield, defined as the ratio of the mols of desired product ($CF_2=CF-SO_2F$) to the reacted mols of the starting product, is of 70%.

EXAMPLE II

By means of modalities identical to those of Example I, 3.15 g (13.5 mmol) of sultone of 2-hydroxy-1-trifluoromethyl-1,2,2-trifluoroethane-sulfonic acid is made flow through a reactant bed constituted by $CaCO_3$, activated as in Example I, maintained at the temperature of 250° C. throughout the test time.

The flowrate of carrier nitrogen stream is kept at 10 litres/hour throughout the test time.

The reaction yield, defined as in Example I, is of 15%.

EXAMPLE III

By following the same modalities as of Example I, but using the sultone of 2-hydroxy-1-pentafluoroethyl-1,2,2-trifluoroethane-sulfonic acid as the starting material, perfluoropropenyl-sulfonyl fluoride is prepared.

What is claimed is:

1. A process for preparing perfluoroalkenyl sulfonyl fluorides having the formula (I)

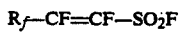

wherein: $R_f$ is selected from the group consisting of F and a perfluoroalkyl radical of from 1 to 9 carbon atoms comprising contacting a β-sultone of a 2-hydroxy-1-perfluoroalkyl-1,2,2-trifluoroethane-sulfonic acid having the formula (II):

(II)

wherein $R_f$ has the meaning defined above, under anhydrous conditions with a reactant selected from the group consisting of oxides and carbonates of an element of Group IA, IIA and IIB, and of the oxides of an element of Group IIIA and IVA of the Periodic Table of the Elements, and their mixtures, at a temperature of from 150° to 450° C., and recovering the desired compound of formula (I) from the reaction effluent.

2. Process according to claim 1 wherein $R_f$ is F.

3. Process according to claim 1 wherein $R_f$ is a perfluoroalkyl radical having from 1 to 3 carbon atoms.

4. Process according to claim 1 carried out continuously under atmospheric pressure.

5. Process according to claim 1 wherein said reactant is selected from the group consisting of CaO, MgO, ZnO, $SiO_2$, $Na_2CO_3$ and $CaCO_3$.

6. Process according to claim 1 wherein the temperature is within the range of from 180° to 280° C.

7. Process according to claim 1 wherein said contacting step is carried out by causing a stream of an inert gas carrier saturated with vapors of said starting sultone to flow on to the reactant.

8. Process according to claim 1 wherein said inert gas carrier is nitrogen.

* * * * *